(12) United States Patent
Inoue et al.

(10) Patent No.: US 10,667,681 B2
(45) Date of Patent: Jun. 2, 2020

(54) VISION TESTING DEVICE

(71) Applicant: CREWT MEDICAL SYSTEMS, INC., Tokyo (JP)

(72) Inventors: Satoshi Inoue, Tokyo (JP); Kenzo Yamanaka, Tokyo (JP); Shinji Kimura, Tokyo (JP)

(73) Assignee: CREWT MEDICAL SYSTEMS, INC., Tokyo (JP)

( * ) Notice: Subject to any disclaimer, the term of this patent is extended or adjusted under 35 U.S.C. 154(b) by 0 days.

(21) Appl. No.: 15/579,875

(22) PCT Filed: May 12, 2016

(86) PCT No.: PCT/JP2016/064120
§ 371 (c)(1),
(2) Date: Dec. 5, 2017

(87) PCT Pub. No.: WO2016/194575
PCT Pub. Date: Dec. 8, 2016

(65) Prior Publication Data
US 2018/0168443 A1 Jun. 21, 2018

(30) Foreign Application Priority Data
Jun. 5, 2015 (JP) ................................. 2015-114503

(51) Int. Cl.
*A61B 3/032* (2006.01)
*A61B 3/024* (2006.01)
(Continued)

(52) U.S. Cl.
CPC ............ *A61B 3/032* (2013.01); *A61B 3/0041* (2013.01); *A61B 3/024* (2013.01); *A61B 3/0075* (2013.01);
(Continued)

(58) Field of Classification Search
CPC ..... A61B 3/032; A61B 3/0008; A61B 3/0033; A61B 3/0041; A61B 3/005; A61B 3/0058;
(Continued)

(56) References Cited

U.S. PATENT DOCUMENTS

| 2016/0270648 A1* | 9/2016 | Freeman | A61B 3/0025 |
| 2016/0324416 A1* | 11/2016 | Fateh | A61B 3/032 |
| 2018/0249151 A1* | 8/2018 | Freeman | G06F 1/163 |

FOREIGN PATENT DOCUMENTS

| JP | H07-67833 A | 3/1995 |
| JP | 2001-037720 A | 2/2001 |

(Continued)

OTHER PUBLICATIONS

Jun. 14, 2016 International Search Report issued in International Patent Application No. PCT/JP2016/064120.

*Primary Examiner* — Marin Pichler
(74) *Attorney, Agent, or Firm* — Oliff PLC (57) ABSTRACT

A vision testing device capable of reducing a psychological sense of uneasiness, stress and the like given to a testee when a vision test is performed with a main body of the vision testing device mounted on a head portion of the testee, including: a device main body mounted on a head portion of a testee who undergoes a vision test, and having display devices for displaying a test image for the testee and a camera for photographing an external image; a switch operated by the testee; and a display control unit which performs switching of display images to be displayed on display devices between a test image and the external image photographed by the camera when the switch is operated under a predetermined operation condition in a state that the test image is displayed on the display devices.

8 Claims, 4 Drawing Sheets

(51) Int. Cl.
*A61B 3/00* (2006.01)
*A61B 3/06* (2006.01)
*A61B 3/18* (2006.01)

(52) U.S. Cl.
CPC ............... *A61B 3/0091* (2013.01); *A61B 3/06* (2013.01); *A61B 3/18* (2013.01)

(58) Field of Classification Search
CPC ......... A61B 3/0075; A61B 3/02; A61B 3/022; A61B 3/024; A61B 3/028; A61B 3/06; A61B 3/063; A61B 3/066; A61B 3/08; A61B 3/09
USPC ....... 351/201, 211, 222, 223, 237, 238, 239, 351/240, 243, 246
See application file for complete search history.

(56) References Cited

FOREIGN PATENT DOCUMENTS

| | | |
|---|---|---|
| JP | 2010-046327 A | 3/2010 |
| JP | 2014-100254 A | 6/2014 |
| JP | 2014-128493 A | 7/2014 |

* cited by examiner

VISION TESTING DEVICE

TECHNICAL FIELD

The present invention relates to a vision testing device used for a vision test.

DESCRIPTION OF RELATED ART

There is a "vision test" as one of eye tests, for testing a visual function of an eye. Also, there is a "visual field test" as a typical vision test. The visual field test is performed for diagnosis of visual field narrowing, visual field defect, and the like caused by, for example, glaucoma, retinal detachment and the like, and various testing devices have been proposed for this purpose.

Further, among conventional vision testing devices, there is a head-mount type vision testing device which is used by being mounted on a testee's head (for example, see patent documents 1 and 2). This type of vision testing device is configured so that a vision test is performed in such a way that a device main body of the vision testing device is mounted on a head portion of a testee, and displaying an image for a test on a display device built in the device main body.

PRIOR ART DOCUMENT

Patent Document
Patent document 1: Japanese Patent Laid Open Publication No. 1995-67833
Patent document 2: Japanese Patent Laid Open Publication No. 2014-128493

SUMMARY OF THE INVENTION

Problem to be Solved by the Invention

Generally, when performing a vision test using a vision testing device, whether or not a visual target displayed (presented) at a predetermined position is visible from the testee is tested, in a state that a fixation target is displayed at a center in a display surface of the display device, to let the testee fixate (gaze) the fixation target. In such a case, only the lights of the fixation target and a visual target are displayed on the display surface of the display device, and other parts are in a very dark display state. Therefore, the testee wearing the device main body of the vision testing device, is placed in the dark where a light is scarcely sensed, and in this state, the testee undergoes a test. Accordingly, there is a problem that the testee who undergoes the visual field test is unaware of the surrounding circumstances and may feel psychological uneasiness and stress.

An object of the present invention is to provide a vision testing device capable of reducing a psychological sense of uneasiness, stress and the like given to the testee when a vision test is performed with the main body of the vision testing device mounted on the head portion of the testee.

Means for Solving the Problem (First Aspect)
According to a first aspect of the present invention, there is provided a vision testing device, including:
a device main body mounted on a head portion of a testee who undergoes a vision test and having display devices for displaying a test image for the testee, and a camera for photographing an external image;
a display control unit which performs switching of display images to be displayed on the display devices between a test image for the vision test and the external image photographed by the camera; and
a switching instruction unit that gives an instruction signal instructing switching of the display images, to the display control unit.

(Second Aspect)
According to a second aspect of the present invention, there is provided the vision testing device of the first aspect, wherein the switching instruction unit is configured using a first operation device operated by the testee at the time of the vision test.

(Third Aspect)
According to a third aspect of the present invention, there is provided the vision testing device of the second aspect, wherein the display control unit performs switching of display images displayed on the display device from the test image to the external image, in a state that the test image is displayed on the display device at the time of operating the first operation device under a predetermined operation condition.

(Fourth Aspect)
According to a fourth aspect of the present invention, there is provided the vision testing device of the third aspect, wherein the first operation device is shared with an operation device operated by the testee for response in the vision test, and
the predetermined operation condition is different from the operation condition set for the response.

(Fifth Aspect)
According to a fifth aspect of the present invention, there is provided the vision testing device of the fourth aspect, wherein a length of time during which the first operation device is pressed is different between an operation condition set for switching the display images and an operation condition set for the response.

(Sixth Aspect)
According to a sixth aspect of the present invention, there is provided the vision testing device of any one of the third to fifth aspects, wherein the display control unit switches the display images from the test image to the external image even when the first operation device is operated under a predetermined operation condition in the middle of the vision test.

(Seventh Aspect)
According to a seventh aspect of the present invention, there is provided the vision testing device of any one of the first to sixth aspects, wherein the switching instruction unit is configured using a second operation device operated by a testee at the time of the vision test.

(Eighth Aspect)
According to an eighth aspect of the present invention, there is provided the vision testing device of any one of the first to seventh aspects, wherein the display control unit has a function of notifying the testee as to which of the test image and the external image is being displayed on the display device.

Advantage of the Invention

According to the present invention, it is possible to reduce psychological uneasiness and stress added on the testee, when a vision test is performed by mounting the main body of the vision testing device on a head portion of the testee.

DETAILED DESCRIPTION OF THE INVENTION

Embodiments of the present invention will be described hereafter, with reference to the drawings.

In the embodiments of the present invention, explanation will be given in the following order.
1. Vision testing device
2. Vision testing method
3. Switching of display images
4. Effect of the embodiment
5. Modified example, etc.

1. Vision Testing Device

Figure 1:
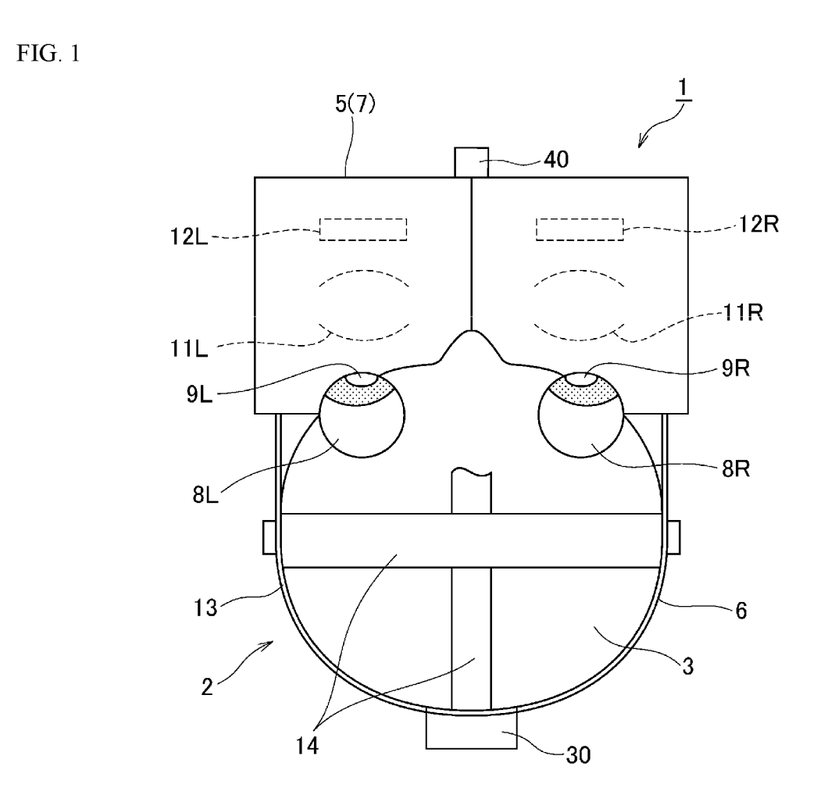
FIG. 1 is a schematic view showing a configuration example of a vision testing device according to an embodiment of the present invention.

FIG. 1 is a schematic view showing a configuration example of a vision testing device according to an embodiment of the present invention. The illustrated vision testing device 1 is a head-mount type vision testing device used by being mounted on a head portion 3 of a testee 2. The vision testing device 1 roughly includes a device main body 5 and a mounting tool 6 mechanically connected to the device main body 5.

The device main body 5 includes a housing 7 having an internal space inside. The internal space of the housing 7 is divided into left and right. The reason is that the vision test is performed separately for a left eye 8L and a right eye 8R of the testee 2. In this vision test, when the left eye 8L is used as the eye to be tested, the testee 2 will see the visual target through a pupil 9L of the left eye 8L, and when the right eye 8R is used as the eye to be tested, the testee 2 will see the visual target through a pupil 9R of the right eye 8R.

The "visual target" described here is displayed to give a stimulus by light to an eyeball of the testee when testing a vision of the testee. With regard to the target, there is no particular limitation on size, shape, and the like. For example, during glaucoma test, it is possible to test (identify) presence or absence of a missing visual field and a location of a defect, by displaying a point of light in a predetermined size as a visual target and changing the position of the point of the light.

In one space of the housing 7, a display optical system 11L and a display device 12L are provided. In the other internal space of the housing 7, a display optical system 11R and a display device 12R are provided. The display optical system 11L and the display device 12L are provided for performing a vision test for the left eye 8L of the testee 2. The display optical system 11R and the display device 12R are provided for performing a vision test for the right eye 8R of the testee 2. A distance between the optical axes of the left and right display optical systems 11L and 11R can be adjusted according to the distance between the pupils of the testee 2 by an adjustment mechanism (not shown).

Further, a camera 40 is installed on the device main body 5. The camera 40 photographs an image (picture) of an outside world (called an external image hereafter). The term "outside world" used here, is a world existing around the testee 2 when the device main body 5 is mounted on the head portion 3 of the testee 2 using the mounting tool 6 described later, and refers to a world that should be visible from the testee 2 unless the device main unit 5 is mounted on the head. Therefore, the image photographed by the camera 40 is a moving image (visible image) representing a state of the outside world in real time. The camera 40 is mounted facing forward in a front portion of the device main body 5 so as to photograph the external image which should exist at the tip of the line of sight of the testee 2.

The mounting tool 6 is provided for mounting the device main body 5 on the head portion 3 of the testee 2. The mounting tool 6 includes a belt 13 wound in a U-shape from both side heads to the back part of the head portion of the testee 2, and a belt 14 wrapped around the top of the head portion of the testee 2. The mounting tool 6 has a mechanism such that the device main body 5 can be firmly fixed and mounted on the head portion 3 of the testee 2 by pulling and tightening the belt 13 from the back part of the head, with a length of the belt 14 adjusted appropriately.

A distance between the optical axes of the display optical systems 11L and 11R, is adjusted in accordance with a distance between pupils in a state that the testee 2 faces the front after the device main body 5 is fixed to the head portion 3 of the testee 2 using the mounting tool 6.

In the following description, in the case of describing the left eye 8L and the right eye 8R of the testee 2 without distinction between left and right, the letters L and R are omitted and they are collectively referred to as the eyeball 8 and the pupil 9. Similarly, in the case of describing the display optical systems 11L and 11R and the display devices 12L and 12R without distinction between for the left eye and for the right eye respectively, the reference symbols L and R are omitted and they are collectively referred to as the display optical system 11 and the display device 12.

(Optical System)

Figure 2:
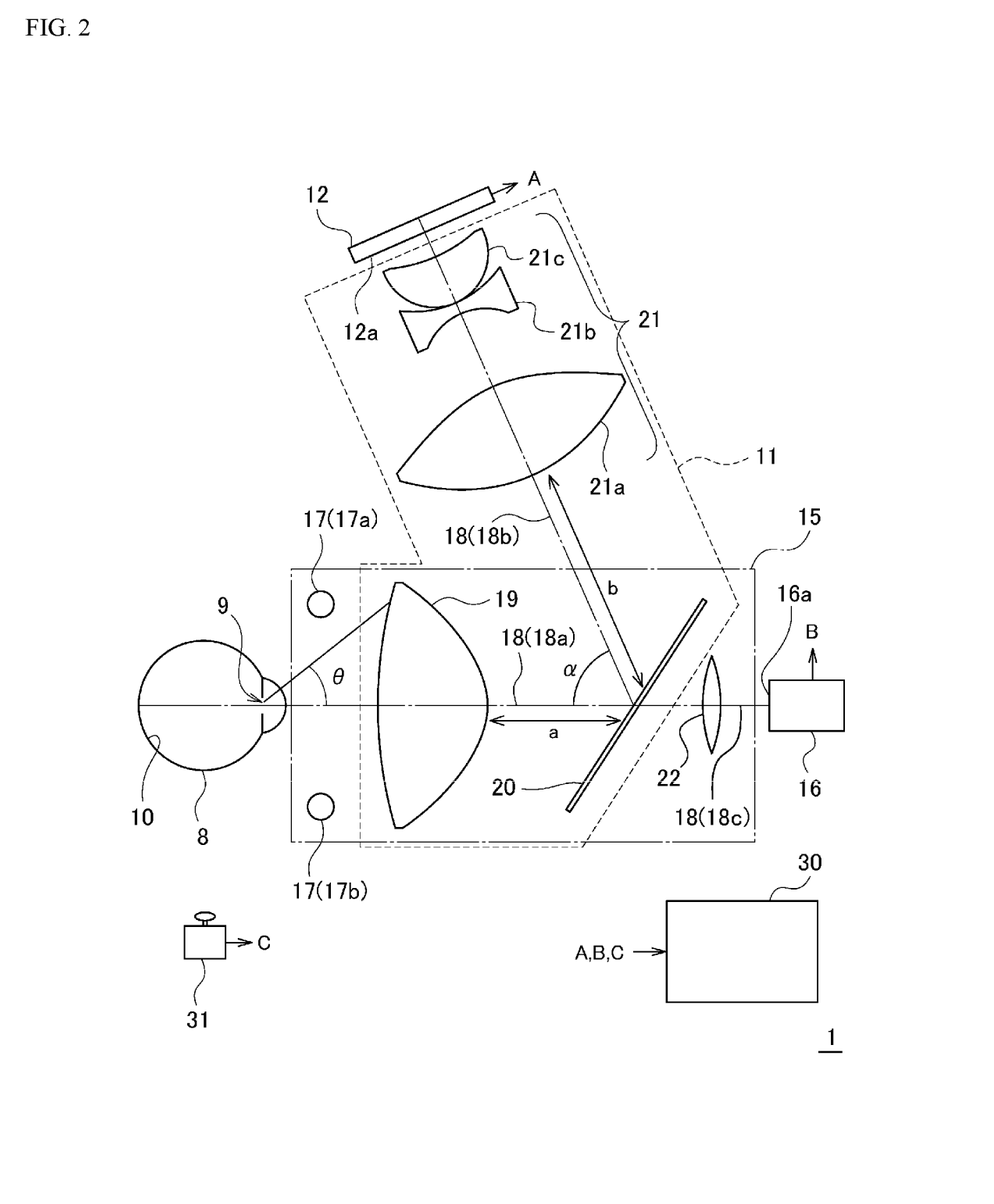
FIG. 2 is a schematic view including a configuration of an optical system of the vision testing device according to an embodiment of the present invention.

FIG. 2 is a schematic view including a configuration of an optical system of the vision testing device according to an embodiment of the present invention.

As shown in the figure, the vision testing device 1 includes: not only the abovementioned display optical system 11 and display device 12, but also an observation optical system 15 for observing the eyeball 8 of the testee, an imaging device 16 for imaging the eyeball 8 of the testee through the observation optical system 15, an infrared light source 17 for irradiating the eyeball 8 of the testee with infrared rays, a control unit 30 that controls an entire vision testing device 1, and a response switch 31. The observation optical system 15, the imaging device 16, and the infrared light source 17, are provided separately for the left eye and the right eye of the testee similarly to the abovementioned display optical system 11 and the display device 12, and one control unit 30 and one switch 31 are provided for each vision testing device 1. The switch 31 is provided as an example of a first operation device operated by the testee who undergoes a vision test. The display device 12, the switch 31, and the imaging device 16 are electrically connected to the control unit 30, respectively as indicated by reference symbols A, B and C in the figure.
(Display Optical System)

The display optical system 11 is provided on an optical axis 18 between an eyeball position where the eyeball 8 of the testee is placed and a display surface 12a of the display device 12. Specifically, the display optical system 11 has a configuration in which a first lens 19, a mirror 20, and a second lens group 21 are arranged in order from the eyeball position side of the testee. Each component will be described below. In the following description, an optical axis from the position of the eyeball to the mirror 20 is taken as an optical axis 18a, and an optical axis from the mirror 20 to the display device 12 is taken as an optical axis 18b, in the optical axes 18 from the eyeball position of the testee to the display device 12.

A first lens 19 is disposed on the optical axis 18a from the eyeball position to the mirror 20. The first lens 19 is formed using an aspheric lens (convex lens) having a positive power. The first lens 19 converges a light reflected by the mirror 20 and incident on the first lens 19, into the pupil 9 of the testee, and suppresses divergence of the light when the testee views an object through the pupil 9 at a wide angle. In FIG. 2, a point of light serving as a visual target is displayed on the display surface 12a of the display device 12, and when the testee views this visual target through the display optical system 11 from the eyeball position, the incident angle of a principal ray incident on the first lens 19 from a pupil center of the testee is indicated by symbol θ. The incident angle θ is an angle with respect to the optical axis 18a (the angle formed by the principal ray passing through the center of the pupil and the optical axis 18a). An outer diameter (diameter) and a position of the first lens 19 on the optical axis 18a are set under a condition so that a visual field angle necessary for the vision test can be secured. Specifically, a maximum visual field angle (the maximum value of θ) of the display optical system 11 using the first lens 19 is preferably not less than 30 degrees and not more than 60 degrees (60 degrees or more and 120 degrees or less in a case of a full field angle) for example.

The mirror 20 is disposed on the optical axis 18a from the eyeball position to the mirror 20 on the side opposite to the eyeball position interposing the first lens 19 therebetween. The mirror 20 is configured using a mirror having wavelength selectivity. Specifically, the mirror 20 is configured using a cold mirror that reflects visible lights and transmits infrared rays. An inclination of a reflecting surface of the mirror 20 with respect to the optical axis 18a is set so that an angle α formed between the optical axis 18a and the optical axis 18b bent by the mirror 20, is preferably not more than 90 degrees, more preferably not more than 80 degrees, still more preferably within a range of "40 degrees<α<70 degrees".

Here, when α≤40°, there is a possibility that the display device 12 and the second lens group 21 are too close to the testee's head portion to interfere with the head portion. On the other hand, when α>40°, it is possible to prevent the display device 12 and the second lens group 21 from interfering with the head portion. On the other hand, when α≥90°, the vision testing device 1 is likely to fall off the head portion when the testee tilts the head forward. On the other hand, when α<90°, the vision testing device 1 is less likely to fall off the head when the testee tilts the head forward.

The second lens group 21 is disposed on the optical axis 18b from the mirror 20 to the display device 12. The second lens group 21 is configured using three lenses 21a, 21b, and 21c. The three lenses 21a, 21b, and 21c are sequentially arranged from the mirror 20 side toward the display device 12 side. That is, the lens 21a is disposed at a position closest to the mirror 20 on the optical axis 18b, and the lens 21c is disposed at a position closest to the display device 12 on the optical axis 18b. Then, the lens 21b is disposed between these two lenses 21a and 21c. The lens 21b is disposed close to the lens 21c in a state of being separated from the lens 21a.

The lens 21a is configured using an aspheric lens (convex lens) having a positive power. Further, the lens 21b is configured using an aspherical lens (concave lens) having a negative power, and the lens 21c is configured using an aspherical lens (convex meniscus lens) having a positive power. The outer diameter (diameter) of the lens 21a is larger than the outer diameters of the other lenses 21b and 21c, and the outer diameters of the lenses 21b and 21c are substantially equal to each other.

Here, when the Abbe number of a material constituting the first lens 19 is v1, the first lens 19 is made of a material (glass, plastic, etc.) satisfying a relational expression "45<v1<80". On the other hand, when the Abbe numbers of the lenses 21a and 21c having a positive power among the lenses 21a to 21c constituting the second lens group 21 are both v2, each of the lens 21a, 21c is made of a material that satisfies the relational expression "45<v2<80". Further, when the Abbe number of the lens 21b having a negative power is v3, the lens 21b is made of a material satisfying the relational expression "15<v3<30".

Further, when a focal length of the first lens 19 is f1 and a focal length of the second lens group 21 is f2, they satisfy the relational expression "0<f1/f2<1.0". Further, the focal length f1 of the first lens 19 is shorter than the sum (a+b) of the optical distance a from the first lens 19 to the mirror 20 and the optical distance b from the mirror 20 to the second lens group 21 (lens 21a).
(Display Device)

The display device 12 is disposed so as to face the lens 21c of the second lens group 21 on the optical axis 18b from the mirror 20 to the display device 12. The display device 12 is configured using, for example, a flat display device such as a liquid crystal display device having a backlight. A display surface 12a of the display device 12 has a configuration in which a large number of pixels are arranged in a matrix. Then, when actually displaying an image (including a visual target) on the display surface 12a, it is possible to control display (on) and non-display (off) of the image on a pixel basis. Further, the display surface 12a of the display device 12 preferably has a display size with a diagonal length of 1.5 inches or less, more preferably a display size with a diagonal length of 1 inch or less, and the optical axis 18b is aligned with a center of the display surface 12a.

In the display optical system 11 and the display device 12 having the above configuration, when the visual target is displayed on the display surface 12a of the display device 12, the testee 2 views the visual target from the eyeball position via the first lens 19, the mirror 20, and the second lens group 21. In such a case, the vision test can be performed in a wider range by increasing the outer diameter of the first lens 19 which is closest to the eyeball position. However, when the outer diameter of the first lens 19 is increased, the principal ray passing through the lens end is greatly inclined with respect to the optical axis 18 (18a). Therefore, when the power of the first lens 19 is low, the principal ray passing through the lens end is diverged.

Therefore, in this embodiment, by using a lens having a high power (preferably a power of 20 D (dioptre) or more and 60 D or less) for the first lens 19, the principal ray passing through the lens end of the first lens 19 is largely refracted and collected in the reflecting surface of the mirror 20. However, when the high power first lens 19 is used as described above, a light flux of the principal ray is converged and focused on the way of an optical path from the first lens 19 to the second lens group 21. Therefore, the second lens group 21 is disposed on the optical axis 18b so that a light flux of the principal ray which is focused on the way of the optical path, is re-converged (imaged) on the display surface 12a of the display device 12. Further, the second lens group 21 is composed of three lenses 21a, 21b, and 21c, in order to correct chromatic aberration and image magnification.

(Observation Optical System)

The observation optical system 15 is provided for observing, for example, an anterior eye part including a pupil 9, an iris, a sclera or the like, a fundus part including the retina 10 or the like, with the eyeball 8 of the testee as an observation target. The observation optical system 15 is provided on the optical axis 18 from the eyeball position of the testee to the imaging device 16. Specifically, the observation optical system 15 has a configuration in which the first lens 19, the mirror 20, and the third lens 22 are arranged in order from the eyeball position side of the testee. Among them, the first lens 19 and the mirror 20, including the optical axis 18a, are common (shared) with the abovementioned display optical system 11. Further, when the optical axis from the mirror 20 to the imaging device 16 is set as the optical axis 18c, the optical axis 18c is substantially parallel to the abovementioned optical axis 18a.

The third lens 22 is disposed on the optical axis 18c from the mirror 20 to the imaging device 16. The third lens 22 is configured using an aspherical lens (convex lens) having a positive power. The third lens 22 is provided for forming an image of a light beam on the imaging surface 16a of the imaging device 16, the light beam being incident on the first lens 19 from the eyeball 8 and passing through the mirror 20, when the eyeball 8 is observed using the first lens 19 as an objective lens.

(Imaging Device)

The imaging device 16 picks up an image of an eyeball (an anterior eye part, a fundus part, etc.) 8, which is a test object. The imaging device 16 is configured using a CCD (Charge Coupled Device) imaging device having sensitivity to infrared rays, a CMOS (Complementary Metal Oxide Semiconductor) imaging device, and the like. The imaging surface 16a of the imaging device 16 is disposed on the optical axis 18c in a direction facing the eyeball 8, and the optical axis 18c is aligned with a center of the imaging surface 16a.

The infrared light source 17 irradiates infrared rays toward the eyeball position of the testee. The infrared light source 17 is configured using a pair of infrared light emitting diodes 17a and 17b. The pair of infrared light emitting diodes 17a and 17b are disposed obliquely above and obliquely downward with respect to the eyeball position of the testee so as not to obstruct a visual field of the testee. Then, one of the infrared light emitting diodes 17a irradiates the eyeball 8 of the testee with infrared rays obliquely from above, and the other infrared light emitting diode 17b irradiates the eyeball 8 of the testee with infrared rays obliquely from below.

In the observation optical system 15 and the imaging device 16 having the above configuration, the image of the eyeball 8 is imaged by the imaging device 16 via the first lens 19, the mirror 20, and the third lens 22, while irradiating the eyeball 8 of the testee with infrared rays from the infrared light source 17.

(Control System)

Figure 3:
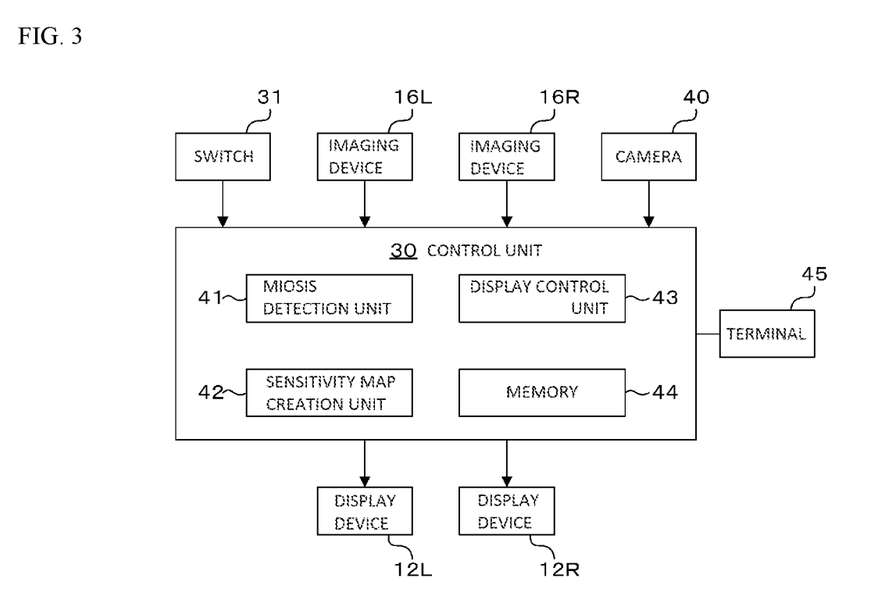
FIG. 3 is a block diagram including a configuration of a control system of the vision testing device according to an embodiment of the present invention.

FIG. 3 is a block diagram including a configuration of a control system of the vision testing device according to an embodiment of the present invention.

The control unit 30 realizes various functions (means) at the time of the vision test. For example, the control unit 30 has a smaller casing structure than the device main body 5, and is attached to the mounting tool 6 at a position corresponding to the back part of the head. Thereby, it is possible to maintain a weight balance in the front and rear of the device main body 5 and the control unit 30.

The control unit 30 is constituted by a computer including a combination of CPU (Central Processing Unit), RAM (Random Access Memory), ROM (Read Only Memory), HDD (Hard Disk Drive), and various interfaces. Then, the control unit 30 is configured so that the CPU realizes various functions by executing a predetermined program stored in a ROM or an HDD. A predetermined program for realizing each function is installed in a computer and used. However, the program may be provided by being stored in a computer readable storage medium, or may be provided through a communication line connected to the computer.

The control unit 30 includes a miosis detection unit 41, a sensitivity map creation unit 42, and a display control unit 43, as an example of a function (means) realized by executing the abovementioned program. Further, the control unit 30 includes a memory 44 as an information storage unit.

The miosis detection unit 41 has a function of detecting a miosis phenomenon of the eye to be tested. The miosis phenomenon is a phenomenon in which the pupil of the testee's eyeball contracts, and occurs when a light enters the pupil of the testee wearing the device main body 5. The miosis detection unit 41 detects the miosis of the pupil 9, when a brightness of the visual target displayed on the display device 12 becomes equal to or higher than a predetermined brightness (luminance), based on the image of the pupil 9 acquired by the imaging device 16.

The sensitivity map creation unit 42 has a function of creating a sensitivity map in a subjective visual field test or an objective visual field test described later. In the subjective visual field test, the sensitivity map creation unit 42 performs mapping, with the brightness (luminance) of the visual target displayed by the display device 12 as the sensitivity of the retina 10, when the testee presses the switch 31 in response to the light of the visual target. Also, in the objective visual field test, the sensitivity map creation unit 42 performs mapping, with the brightness (luminance) of the visual target displayed by the display device 12 as the sensitivity of the retina 10, when the miosis detecting unit 41 detects the miosis of the pupil 9.

The display control unit 43 has a function of controlling an image to be displayed on the display device 12. The image to be displayed on the display device 12 (hereinafter also referred to as "display image") is roughly divided into two parts. One is a test image for vision test and the other is an image of the outside world (external image) photographed by the camera 40. For example, the display control unit 43 displays the test image on the display element 12 according to an instruction given from the terminal 45. The test image includes: not only the image including the fixation target and the visual target displayed to the testee at the time of the visual field test, but also an image for making the testee's eyes accustom to the dark. As one form of display control, the display control unit 43 performs control to switch the display image displayed on the display element 12, between the test image and the external image. At this time, the display control unit 43 switches the display image to be displayed on the display device 12, from the test image to the external image, or from the external image to the test image, in accordance with an instruction signal given from a switching instruction unit described later.

The memory 44 is used to store various kinds of information including information necessary for the vision test. For example, the sensitivity map creation unit 42 sequentially stores test results in the memory 44, the test results being obtained from the start of the vision test until the end of the vision test, and creates a sensitivity map using the test results stored in the memory 44, after end of the vision test.

In addition to the switch 31, the imaging devices 16L and 16R, the camera 40, and the display devices 12L and 12R, a terminal 45 is connected to the control unit 30 so as to be wired or wirelessly communicable. The terminal 45 is provided as an example of a second operation device operated by a tester who performs the vision test. The terminal 45 is operated for performing various settings, adjustments, instructions, and the like necessary for the vision test, to the control unit 30 by an ophthalmologist who performs the vision test, or the tester such as a nurse or a caregiver who assists the ophthalmologist. The terminal 45 is configured using, for example, a personal computer with a monitor.

The switch 31 is operated for response by the testee mainly in the vision test. In this embodiment, a switching instruction unit is configured using this switch 31. The switching instruction unit gives an instruction signal instructing switching of display images, to the display control unit 43. As the switch 31, preferably, a manually operated switch which the examinee holds by manually, more preferably a push-type switch which the examinee presses with a finger (for example, a thumb or an index finger) may be used. In this case, when the testee presses the switch 31, the switch 31 is switched from OFF state to ON state, and ON signal is outputted from the switch 31. This ON signal is taken into the control unit 30. Therefore, the control unit 30 can detect (recognize) whether the switch 31 is in ON state (pressed state) or OFF state depending on whether or not an ON signal is outputted from the switch 31.

2. Vision Testing Method

Subsequently, a vision testing method performed using the vision testing device 1 according to the embodiment of the present invention will be described.

First, in order to perform the vision test, as shown in FIG. 1, the device main body 5 is required to be mounted on the head portion 3 of the testee 2 using the mounting tool 6 before the vision test. At this time, for example, when the position of the eyeball 8 of the testee 2 is previously deviated from a presumed regular position, by mounting the device main body 5 in an inclined state, there is a possibility that a correct test result cannot be obtained in the vision test. Therefore, when the device main body 5 is mounted on the testee 2, a work of adjusting the position of the device main body 5 is performed so that the position of the eyeball 8 matches a regular position. The position adjustment of the device main body 5 is performed after adjusting the distance between the optical axes of the display optical system 11 in accordance with the distance between the pupils of the testee 2. Further the position adjustment of the device main body 5 is performed by using image data of the eyeball 8 photographed by the imaging device 16. Specifically, for example, the image of the eyeball 8 photographed by the imaging device 16 is displayed together with the alignment mark on the monitor of the terminal 45, and on the monitor, the position of the device main body 5 is adjusted so that the pupil 9 of the testee 2 matches the alignment mark.

In the vision testing device 1 according to the embodiment of the present invention, it is possible to perform dynamic quantitative visual field examination (Goldman visual field examination), static quantitative visual field examination, fundus visual field examination (microperimetry), electroretinogram (ERG) and other examination. Here, as an example, a case of performing static quantitative visual field examination will be described.

The static quantitative visual field examination is performed as follows. First, a fixation target is presented at a center of the visual field, to let the testee fixate the fixation target. Next, while letting the testee fixate the fixation target, the visual target is presented at one point in the visual field, and its brightness is gradually increased. Then, when the brightness of the visual target reaches a certain level, the visual target becomes visible from the testee. Therefore, a value corresponding to the brightness at the time when the testee can see the visual target is set as a retina sensitivity at the point of presenting the visual target at that time. Then, by performing similar measurement for each point in the visual field, the retina sensitivity within the visual field is quantitatively investigated, to thereby create a map. Such static quantitative visual field examination includes a subjective visual field test and an objective visual field test. By using the vision testing device 1 of this embodiment, it is possible to perform any type of test. Explanation will be given hereafter.

The subjective visual field test is performed as follows. First, the head mount-type vision testing device 1 (device main body 5) is mounted on the testee's head, and the switch 31 is held in the hand of the testee. Next, based on the instruction of the control unit 30, the fixation target is displayed at the center portion of the display surface 12a of the display device 12 to let the testee fixate the fixation target, and in this state, the visual target for the visual field test is displayed at one point on the display surface 12a. At this time, at first, the brightness of the visual target is made dark, and thereafter, the brightness of the visual target is gradually increased. Then, even if it is dark at the beginning and the visual target is not visible from the testee, when the brightness of the visual target reaches a certain level, the retina of the testee responds to a light stimulus, and the visual target becomes visible from the testee. Therefore, when the visual target becomes visible from the testee, the testee is asked to press the switch 31 as a response. When the testee presses the switch 31, an ON signal is sent to the control unit 30. Upon receipt of this ON signal, the sensitivity map creation unit 42 sets a value corresponding to the brightness of the target point at that time as the sensitivity of the retina at that point. Thereafter, similar measurement is performed for each point in the visual field, whereby the sensitivity map creation unit 42 quantitatively investigates a difference in retina sensitivity within the visual field, to thereby create a retina sensitivity map.

The objective visual field inspection is performed as follows. First, the head mount-type vision testing device 1 is mounted on the testee's head, to let the testee fixate the fixation target in the same manner as described above. Next, the visual target for visual field test is displayed at one point on the display surface 12a of the display device 12 based on an instruction from the control unit 30. At this time, the brightness of the vision target is made dark at first, and thereafter, the brightness of the vision target is gradually increased. Then, even when the visual target is not visible from the testee at first, when the brightness of the visual target reaches a certain level, the retina of the testee responds to the light stimulus, and the visual target becomes visible from the testee.

At that time, the size (pupil diameter) of the pupil 9 of the testee changes according to the brightness of the visual target. Specifically, the diameter of the pupil 9 of the testee is reduced. A state change of the eyeball 8 at this time is imaged. The imaging of the eyeball 8 is performed in such a manner that infrared light is irradiated from an infrared light source 17 toward the eyeball 8 and the image light of the eyeball 8 obtained thereby is imaged on the imaging surface 16a of the imaging device 16 via an observation optical system 15 (19, 20, 22). The timing at which the imaging of the eyeball 8 is started may be set, for example, at the timing before displaying the visual target on the display surface 12a, or at the same time as displaying the visual target. Incidentally, since the human retina is not sensitive to infrared rays, it does not affect the state change of the eyeball 8.

The image data of the eyeball 8 imaged using the imaging device 16 is taken in the control unit 30. At this time, in the miosis pupil detection unit 41, in the process of gradually increasing the brightness of the visual target, whether the pupil diameter of the testee has changed (reduced) in response to the brightness of the visual target is determined based on the image data sent from the imaging device 16. Then, when the pupil detection unit 41 determines that the pupil diameter of the testee has changed, the sensitivity map creation unit 42 sets a value corresponding to the brightness at the point of the visual target at that time as the sensitivity on the retina at that point. Thereafter, by automatically performing similar measurements one after another at each point in the visual field, the sensitivity map creation unit 42 quantitatively examines a difference of sensitivity on the retina in the visual field and automatically creates a sensitivity map on the retina.

In addition, in the objective visual field test, a single threshold upper stimulation method may be used, which is a method of creating a sensitivity map by displaying a bright visual target at one point on the display surface 12a of the display device 12 and observing a degree of reduction in the pupil diameter.

3. Switching of Display Images

Switching of display images performed by the display control unit 43 will be described next.

First, when the switch 31 is operated under a predetermined operation condition while the test image is being displayed on the display device 12, the display control unit 43 switches the display image to be displayed on the display device 12 from the test image to the external image. The "predetermined operation condition" described here is the operation condition set for switching display images, and is different from the operation condition set for response when the testee 2 senses the light of the visual target in the vision test. When the switch 31 is actually pressed, the display control unit 43 judges whether the operation at that time conforms to the operation condition for switching display images or conforms to the operation condition for response, depending on a length of the time during which the testee is pressing the switch 31.

The switch 31 outputs an ON signal only when pressed by the testee, and is set in an OFF state when it is not pressed. Therefore, the time during which the switch 31 continues to output the ON signal is defined as "ON duration time" here. In such a case, the display control unit 43 controls switching of display images in accordance with a processing procedure shown in FIG. 4. A main component that executes the processing of each step in the figure is the display control unit 43.

Figure 4:
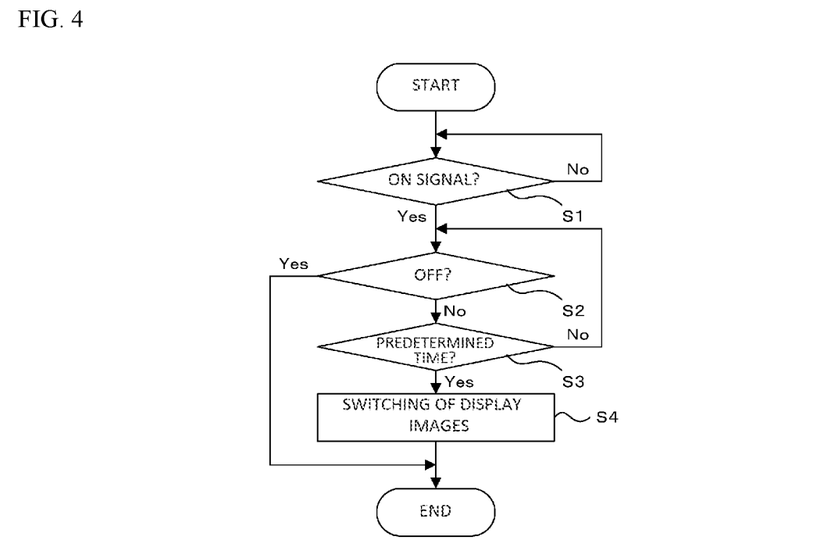
FIG. 4 is a flowchart showing a processing procedure relating to switching of display images.

First, in step S1, whether or not the switch 31 outputs the ON signal is judged. Then, when it is judged that the switch 31 outputs the ON signal, the processing proceeds to the next step S2.

In step S2, whether or not the switch 31 is set in an OFF state is judged. When it is judged that the switch 31 is set in the OFF state, a series of processing is ended as it is. On the other hand, when the switch 31 is not set in the OFF state, that is, when the ON signal is continuously outputted from the switch 31, the processing proceeds to step S3.

In step S3, whether or not the abovementioned ON duration time reaches a predetermined time (for example, 3 seconds) is judged. When the ON duration time does not reach the predetermined time, the processing returns to step S2.

On the other hand, when the ON duration time reaches the predetermined time, the processing proceeds to step S4, and there, switching of display images is performed, and a series of processing is ended.

As described above, in this embodiment, whether or not the switch 31 is operated under the predetermined operation condition is determined based on the ON duration time. Then, the display control unit 43 controls the switching of display images in accordance with the abovementioned processing procedure, every time the switch 31 is pressed.

Namely, when the operation of pressing the switch 31 is canceled before the ON duration time reaches the predetermined time, it is judged that the switch 31 is not operated under the predetermined operation condition, and switching of display images is not performed. In this case, the ON signal outputted from the switch 31 conforms to the operation condition for response (ON duration time<predetermined time).

Therefore, when the ON signal conforming to the operation condition is sent to the control unit 30 during the visual field test, the sensitivity map creation unit 42 recognizes the ON signal as a response signal indicating that the testee 2 has sensed the light of the visual target, and a value corresponding to the brightness at the point of the visual target at that time as the sensitivity on the retina at that point.

Further, when the switch 31 is pressed until the ON duration time reaches the predetermined time, the display control unit 43 judges that the switch 31 is operated under the predetermined operation condition, and performs switching of display images. In this case, the ON signal outputted from the switch 31 is an instruction signal that conforms to the operation condition for switching display images (ON duration time≥predetermined time), that is, an instruction signal instructing the switching of the display images, and this instruction signal is given to the display control unit 43.

Therefore, when the ON signal conforming to such an operation condition is sent to the control unit 30, the display control unit 43 recognizes the ON signal as the instruction signal of switching display images even during the visual field test, and immediately switches the display image from the test image to the external image.

When the display control unit 43 performs switching of display images, the testee can visually recognize the switching of display images, but there is a possibility that the tester tries to proceed with the test without knowing the fact. In response to such a case, the display control unit 43 may have a function of notifying the tester of a current display state. The current display state refers to the following state: which of the test image and the external image is being displayed on the display device 12. As a method of a specific notification to the tester, various methods such as notification by display, notification by sound, notification by light, notification by vibration, or notification by suitable combination of them, and the like can be considered.

Specific examples are as follows. As a method of notification by display, it is conceivable to display the current display state on the monitor of the terminal 45 operated by the tester as an image, a message or the like. As a method of notification by sound, it is conceivable to output sound from a speaker provided in the terminal 45 or output sound as a warning sound. As a method of notification by light, it is conceivable to provide a lamp in the device main body 5, the terminal 45, or both, and changes a lighting state (on/off state) of the lamp and the color of the lamp to be lit depending on which of the test image and the external image is displayed on the display device 12. As a method of notification by vibration, it is conceivable to vibrate the terminal 45 operated by the tester when the display image displayed on the display element 12 is switched from the test image to the external image.

Further, when the display image is switched (returned) from the external image to the test image, for example, the following various methods are conceivable regarding the timing of switching display images. For example, the following methods are conceivable. One of them is a method of switching at the timing when the pressed state of the switch 31 is canceled. The other method is a method of switching at the timing when the switch 31 is operated again under a predetermined operation condition after the pressed state of the switch 31 is canceled. In this case, every time the switch 31 is operated under the predetermined operation condition, the display control unit 43 alternately switches the display image from the test image to the external image.

4. Effect of Embodiment

Hereinafter, effects of the embodiment of the present invention will be described with specific states.

First, in a state in which the device main body 5 is mounted on the testee 2, the testee 2 is placed in the darkness closed from the outside world even if a fixation target is displayed on the display device 12. Therefore, in addition to a psychological uneasiness that the testee 2 who is wearing the device main body 5 receives a vision test from now on, the testee 2 is likely to feel the feeling of anxiety and stress that surrounding circumstances are completely unknown. Particularly, such a feeling of anxiety is increased when a person other than the tester is around the testee 2 or when the testee 2 puts valuable items and other baggage close to the testee 2.

In such a case, if the testee 2 can visually confirm the state of the outside world with his own will, the feeling of the anxiety and stress felt by the testee 2 is greatly alleviated. However, when the device main body 5 is detached in the middle of the vision test in order to let the testee 2 confirm the state of the outside world, it is necessary to readjust the position of the device main body 5 when the device main body 5 is mounted again. Further, even when the position of the device main body 5 is adjusted after the device main body 5 is mounted again, it is difficult to accurately reproduce a mounted state before detachment. Therefore, when the device main body 5 is detached during the vision test, there is a possibility that a test condition such as an eyeball position is changed after detachment.

Therefore, prior to the start of the vision test, the tester notifies the testee 2 of how to operate the switch 31 when the device main body 5 is mounted on the head portion 3 of the testee 2. Specifically, for example, when the testee 2 feels that the visual target is visible in visual field test, the tester tells the testee 2 to push the switch 31 briefly at that moment. Further, when the testee 2 wants to confirm the state of the outside world, the tester tells the testee 2 that the external image is displayed on the display device 12 by pressing the switch 31 long (press and hold the switch 31). Further, the tester tells the testee 2 to actually press and hold the switch 31 for long pushing to confirm the external image displayed on the display element 12. As a result, the testee 2 can face a vision test in a state that psychological uneasiness and stress are reduced.

Further, in the vision testing device of the type that the testee looks into, by looking inside in a state of a near vision of the testee, the problem of myopia of the device occurs. On the other hand, the fixation target and the visual target displayed on the display element 12 are displayed at a presentation distance longer than a distance seen by near vision (around 30 cm). Therefore, when the myopia of the device occurs, the fixation target displayed on the display device 12 sometimes appears blurred even by a testee having normal visual acuity. When this blur is solved, for example, by performing diopter adjustment by moving a lens of the display optical system 11, the vision test will be performed while leaving an influence of the myopia of the device. Therefore, there is a possibility that an accurate test result cannot be obtained.

In that respect, when the switch 31 is operated by the testee 2 under a predetermined operation condition prior to the start of the vision test, thereby displaying the external image on the display element 12, the testee can grasp the state of the surrounding circumstances and can feel a sense of security while at the same time the tension of the crystalline lens by the myopia of the device is solved and its influence can be reduced. Accordingly, it is possible to simultaneously reduce the psychological anxiety and stress of the testee and effect of the myopia of the device.

Further, in this embodiment, even when the testee operates the switch 31 under a predetermined operation condition during the vision test, the display control unit 43 immediately performs switching of display images from the test image to the external image. Therefore, the testee can confirm the state of the outside world at any time by his own intention, not only before starting the vision test but also during the vision test. Accordingly, by allowing the tester to previously inform the testee of that fact, it is possible to reduce a mental burden of the testee who faces the vision test. Further, even when the testee feels tired in the middle of the vision test, the testee can take a moderate rest by switching the display image to the external image without detaching the device main body 5. Further, even when a sound of a fire truck siren or the like is heard at the ear of a testee who is undergoing vision test and the sound is gradually increased, the testee can quickly confirm the surrounding circumstances (especially safety etc.) only by operating the switch 31.

Further, since the switch 31 is shared for the display image for switching and for response, the testee can switch the display image without changing the switch 31 even during the vision test. Accordingly, for example, even in an emergency such as an occurrence of an earthquake, the testee can instantaneously operate the switch 31 to switch the display image to the external image.

Further, even when the testee switches a display screen by operating the switch 31, there is no change in a state of mounting the device main body 5. Therefore, the test condition such as a position of the eyeball can be prepared before switching the display image from the test image to the external image and after returning the display image from the external image to the test image. Accordingly, the vision test can be restarted without readjusting the position of the device main body 5. Further, the test result obtained before switching the display image from the test image to the external image and the test result obtained after returning the display image from the external image to the test image, are collected as one test result, and it is also possible to create a retina sensitivity map and the like. Therefore, the test result obtained in the middle of the vision test can be effectively utilized without waste.

5. Modified Example, Etc.

The technical scope of the present invention is not limited to the embodiment described above and includes various modes and modifications as far as the specific effects obtained by the constituent features of the invention and combinations thereof can be derived.

For example, in the abovementioned embodiment, the switch for switching display images and the switch for response in the vision test are shared, but the present invention is not limited thereto, and they may be constituted by separate switches.

Further, in the abovementioned embodiment, when the ON signal of the switch 31 operated by the testee continues for a predetermined time or longer, the ON signal is recognized as an instruction signal for switching the display image, and the display control unit 43 switches the display image. However, the present invention is not limited thereto, and for example, a switching instruction unit may be configured using the terminal 45 operated by the tester. Further, both the switch 31 and the terminal 45 may be used to configure the switching instruction unit.

When the switching instruction unit is configured using the terminal 45, the terminal 45 sends the instruction signal to the control unit 30 when the tester performs a predetermined operation to thereby switch the display image, and the display control unit 43 may switch the display image upon receipt of the switching instruction signal. As a result, even when the testee is older and it is difficult to memorize the operation method of the switch 31, or when the switch 31 cannot be properly operated in accordance with predetermined operation condition, the tester can switch the display image while listening to the state and a desire of the testee. Therefore, even the testee who is unfamiliar with the operation of the switch 31 can receive the vision test with confidence.

Further, in the abovementioned embodiment, the liquid crystal display device is used to constitute the display element 12. However, the present invention is not limited thereto, and an organic EL (Electro Luminescence) display device may be used.

Further, in the abovementioned embodiment, the display optical system 11 is composed of four lenses in total, and the observation optical system 15 is composed of two lenses in total (one of which is shared with the display optical system 11). However, the number and the shape of the lenses constituting each optical system, a lens interval in the optical axis direction, and the like can be changed as necessary.

However, the second lens group 21 corrects chromatic aberration and image magnification by combining a lens having a positive power and a lens having a negative power, and therefore the second lens group 21 is preferably composed of a plurality of lenses. Further, the mirror 20 may be formed by a dichroic mirror.

Figure 5:
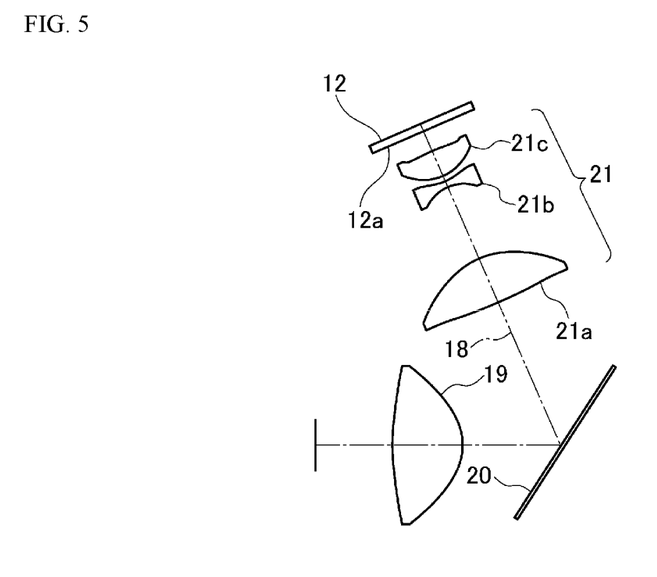
FIG. 5 is a schematic view (No. 1) showing another configuration example of a display optical system.
Figure 6:
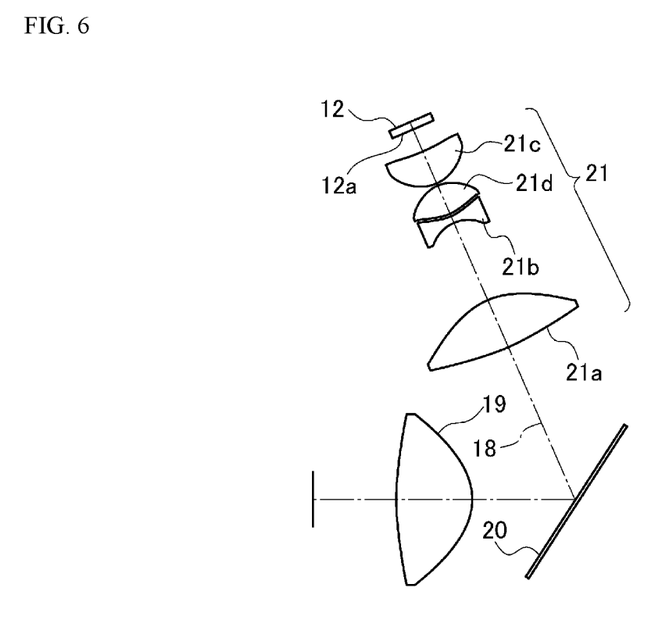
FIG. 6 is a schematic view (part 2) showing another configuration example of a display optical system.

As an example, other configuration example of the display optical system is shown in FIG. 5 and FIG. 6.

In FIG. 5, the lens 21c belonging to the second lens group 21 of the display optical system 11 is made movable in the optical axis direction by a lens moving mechanism (not shown), which is different from the above embodiment. When this configuration is adopted, the diopter can be adjusted according to the visual acuity of the testee.

In contrast, in FIG. 6, the second lens group 21 of the display optical system 11 is configured using four lenses 21a to 21d in total by adding the lens (convex lens) 21d and the size of the display surface 12a of the flat display element 12 is reduced, which are different from the above embodiment. When this configuration is adopted, it becomes possible to display the visual target more clearly for the testee. Further, in this configuration as well, by making the lens 21c movable in the direction of the optical axis, it becomes possible to adjust the diopter according to the visual acuity of the testee.

DESCRIPTION OF SIGNS AND NUMERALS

1 Vision testing device
2 Testee
3 Head portion
5 Device main body
6 Mounting tool
8 Eyeball
9 Pupil
11 Display optical system
12 Display device
12a Display surface
15 Observation optical system
16 Imaging device
30 Control unit
31 Switch
40 Camera
43 Display control unit

The invention claimed is:

1. A vision testing device comprising:
   a housing configured to be mounted on a head of a testee, the housing including an internal space;
   a set of display devices configured to display a test image for the testee to view within the internal space;
   a camera installed on the housing, the camera being configured photograph an external image in a line of sight of the testee;
   a processor configured to switch display images displayed on the set of display devices between the test image for a vision test and the external image photographed by the camera during the vision test; and
   a switch configured to send an instruction signal to the processor to switch the display images.

2. The vision testing device according to claim 1, wherein the switch is configured be operated by the testee during the vision test.

3. The vision testing device according to claim 2, wherein the processor is configured to switch the display images displayed on the set of display devices from the test image to the external image in response to the test image being displayed on the set of display devices and the switch being operated with a first predetermined operation condition.

4. The vision testing device according to claim 3, wherein the switch is configured to receive a response from the testee based on the vision test, the response being operated with a second predetermined operation condition, and the first predetermined operation condition is different from the second predetermined operation condition.

5. The vision testing device according to claim 4, wherein the first predetermined operation condition includes a different length of time during which the switch is operated than a length of time of the second predetermined operation condition.

6. The vision testing device according to claim 3, wherein the processor is configured to switch the display images from the test image to the external image in response to the switch being operated with the first predetermined operation condition during the vision test.

7. The vision testing device according to claim 1, wherein the switch is also configured to be operated by a tester during the vision test.

8. The vision testing device according to claim 1, wherein the processor is configured to notify a tester as to which one of the test image and the external image is displayed on the set of display devices.

* * * * *